(12) United States Patent
West

(10) Patent No.: US 7,942,894 B2
(45) Date of Patent: May 17, 2011

(54) EMBOLIC DEVICE DELIVERY SYSTEM

(75) Inventor: Stephen West, Pembroke Pines, FL (US)

(73) Assignee: Codman & Shurtleff, Inc., Raynham, MA (US)

( * ) Notice: Subject to any disclaimer, the term of this patent is extended or adjusted under 35 U.S.C. 154(b) by 357 days.

(21) Appl. No.: 11/345,005

(22) Filed: Jan. 31, 2006

(65) Prior Publication Data
US 2007/0179520 A1    Aug. 2, 2007

(51) Int. Cl.
A61M 29/00    (2006.01)

(52) U.S. Cl. ........ 606/200; 606/108; 606/198; 606/151; 294/99.1; 294/99.2

(58) Field of Classification Search ........... 606/200, 606/108, 198, 907, 205–206, 151; 623/1.23, 623/1.11; 294/99.1, 99.2, 200
See application file for complete search history.

(56) References Cited

U.S. PATENT DOCUMENTS

| | | | | |
|---|---|---|---|---|
| 1,294,284 A * | 2/1919 | Logeman | | 606/210 |
| 2,549,731 A * | 4/1951 | Wattley | | 439/482 |
| 2,638,365 A | 5/1953 | Jones | | |
| 3,429,408 A | 2/1969 | Maker | | |
| 4,655,219 A * | 4/1987 | Petruzzi | | 606/206 |
| 5,108,407 A | 4/1992 | Geremia et al. | | |
| 5,217,438 A | 6/1993 | Davis et al. | | |
| 5,217,484 A * | 6/1993 | Marks | | 606/200 |
| 5,234,437 A | 8/1993 | Sepetka | | |
| 5,250,071 A * | 10/1993 | Palermo | | 606/198 |
| 5,261,916 A * | 11/1993 | Engelson | | 606/108 |
| 5,263,964 A * | 11/1993 | Purdy | | 606/200 |
| 5,304,195 A * | 4/1994 | Twyford et al. | | 606/191 |
| 5,354,295 A * | 10/1994 | Guglielmi et al. | | 606/32 |
| 5,571,089 A | 11/1996 | Crocker | | |
| 5,725,546 A | 3/1998 | Samson | | |
| 5,746,769 A * | 5/1998 | Ton et al. | | 606/206 |
| 5,765,449 A | 6/1998 | LeMire | | |
| 5,782,747 A * | 7/1998 | Zimmon | | 600/104 |
| 5,895,391 A * | 4/1999 | Farnholtz | | 606/108 |
| 5,895,411 A * | 4/1999 | Irie | | 606/213 |

(Continued)

FOREIGN PATENT DOCUMENTS

EP    1 537 838 A    6/2005

OTHER PUBLICATIONS

European Search Report issued in European Application No. EP 07 25 0341 dated May 8, 2007.

*Primary Examiner* — Darwin P Erezo
*Assistant Examiner* — Mark Mashack
(74) *Attorney, Agent, or Firm* — Cook Alex Ltd.

(57) ABSTRACT

A vascular occlusion device deployment system is provided for deploying an embolic device at a preselected site within the vasculature of a patient. The deployment system includes a tubular element having a catch movably located within the tubular element. The catch has a normal open configuration and a closed configuration. When in the closed configuration, the catch grasps a headpiece of an embolic device. The tubular element has a constraining section and a releasing section. When the catch is within the constraining section of the tubular element, the constraining section acts upon the catch to keep the catch in a closed configuration. When the catch is moved to the releasing section, the catch returns to its normally open configuration and releases its grasp of the embolic device headpiece.

10 Claims, 4 Drawing Sheets

U.S. PATENT DOCUMENTS

| | | | |
|---|---|---|---|
| 5,989,242 A * | 11/1999 | Saadat et al. | 606/1 |
| 6,190,373 B1 * | 2/2001 | Palermo et al. | 606/1 |
| 6,203,547 B1 | 3/2001 | Nguyen et al. | |
| 6,277,125 B1 * | 8/2001 | Barry et al. | 606/108 |
| 6,296,622 B1 * | 10/2001 | Kurz et al. | 604/93.01 |
| 6,478,773 B1 | 11/2002 | Gahndi et al. | |
| 6,561,988 B1 * | 5/2003 | Turturro et al. | 600/564 |
| 6,562,064 B1 * | 5/2003 | deBeer | 623/1.12 |
| 6,797,001 B2 * | 9/2004 | Mathis et al. | 623/2.37 |
| 6,849,081 B2 * | 2/2005 | Sepetka et al. | 606/213 |
| 7,201,768 B2 * | 4/2007 | Diaz et al. | 623/1.11 |
| 7,473,266 B2 * | 1/2009 | Glaser | 606/213 |
| 7,582,101 B2 * | 9/2009 | Jones et al. | 606/200 |
| 7,708,755 B2 * | 5/2010 | Davis et al. | 606/200 |
| 2002/0099408 A1 | 7/2002 | Marks et al. | |
| 2002/0151915 A1 * | 10/2002 | Hieshima et al. | 606/157 |
| 2004/0073230 A1 * | 4/2004 | Mulholland et al. | 606/108 |

* cited by examiner

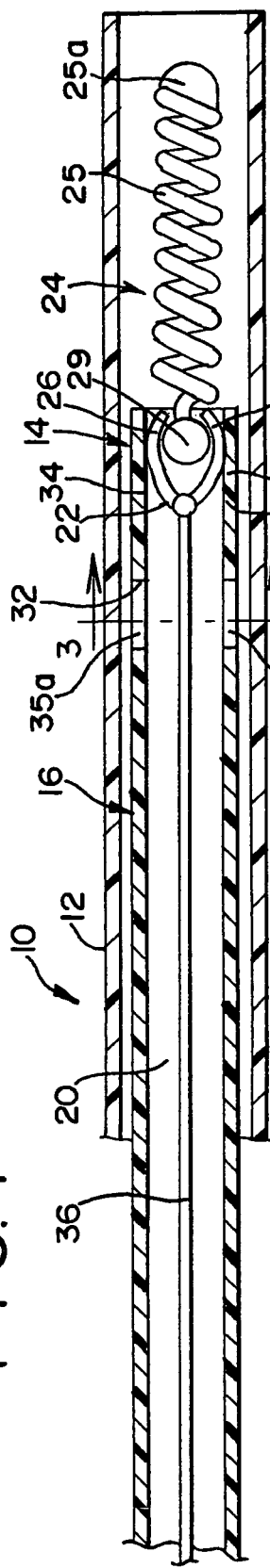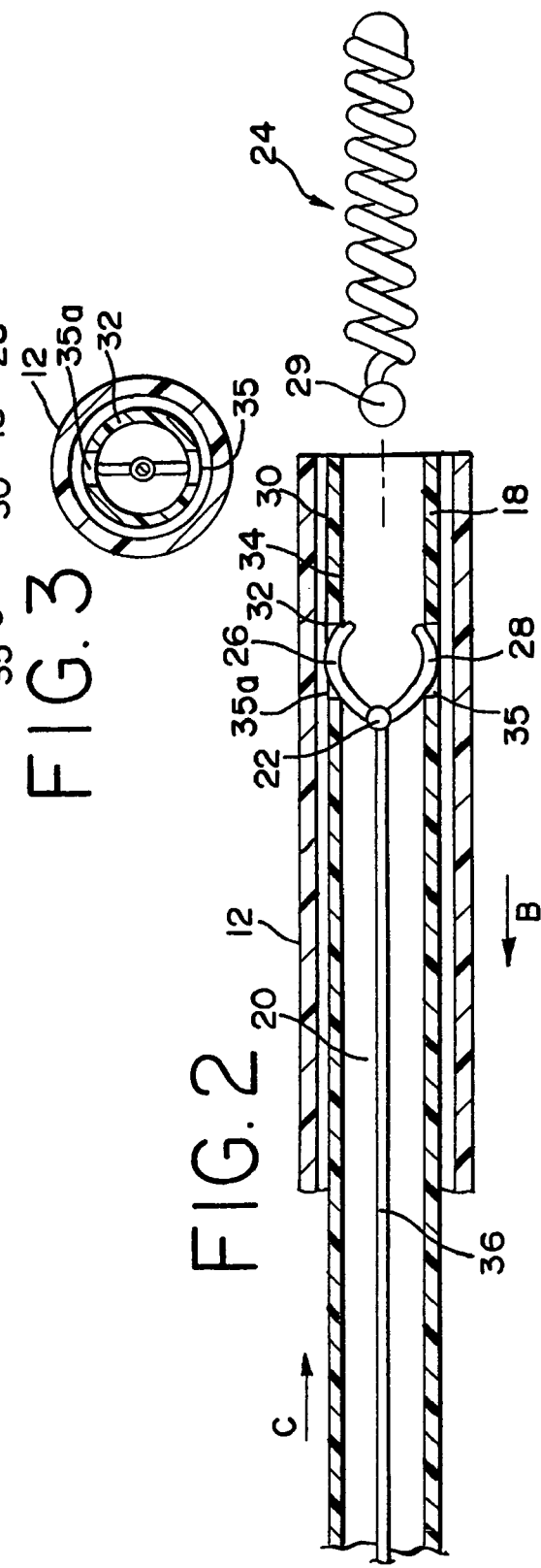

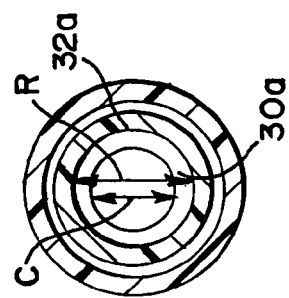
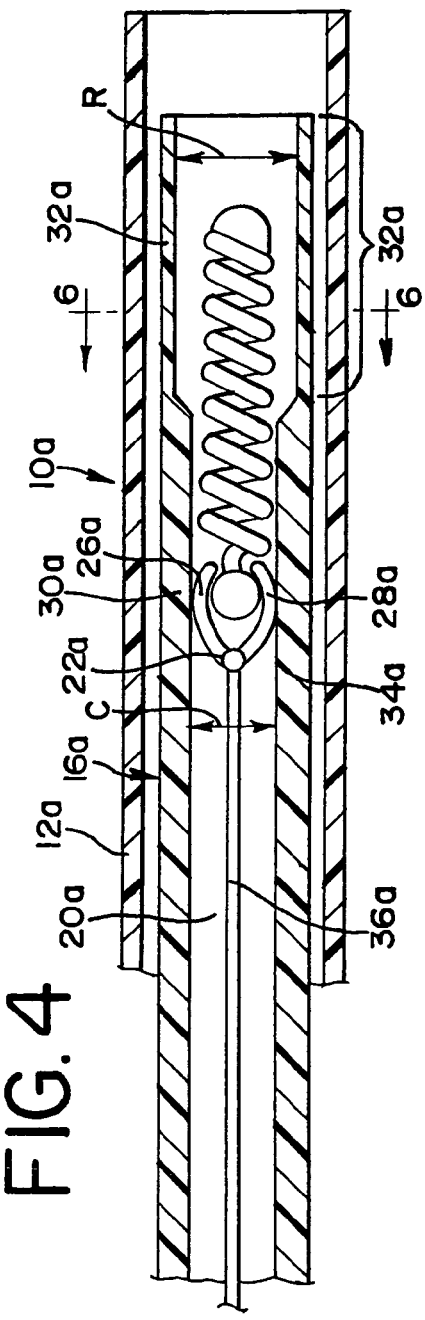
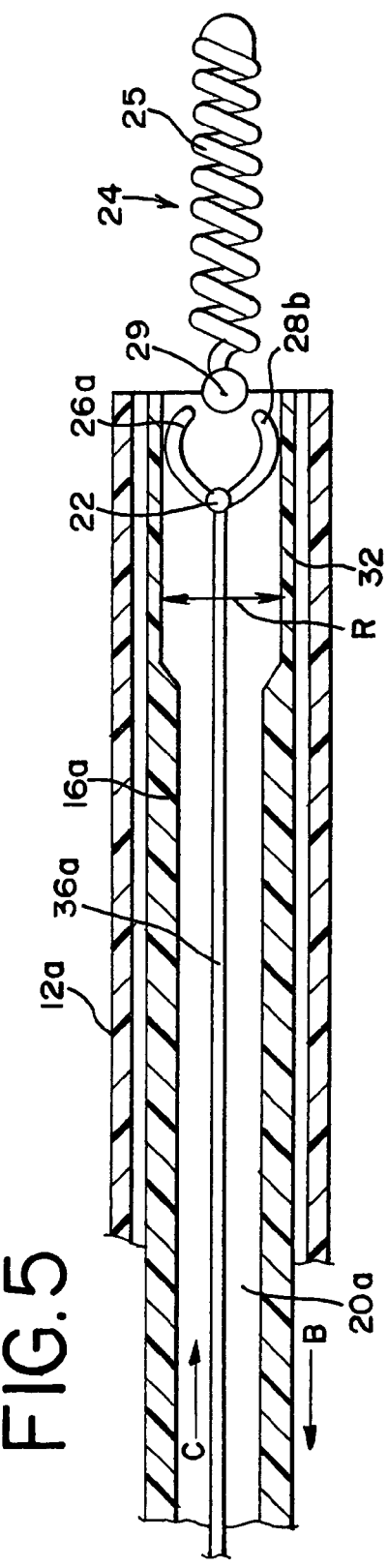

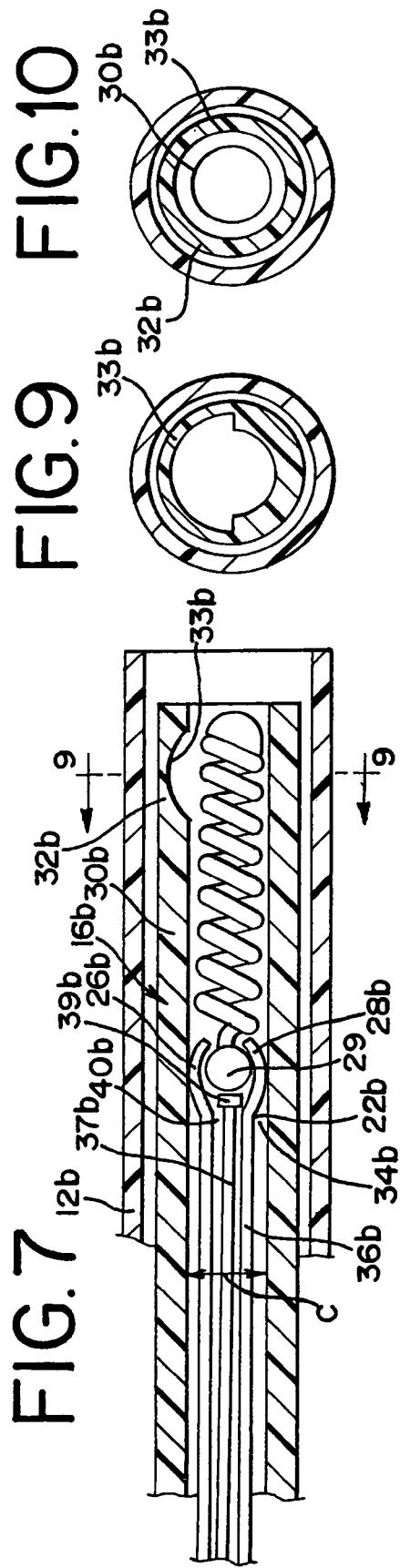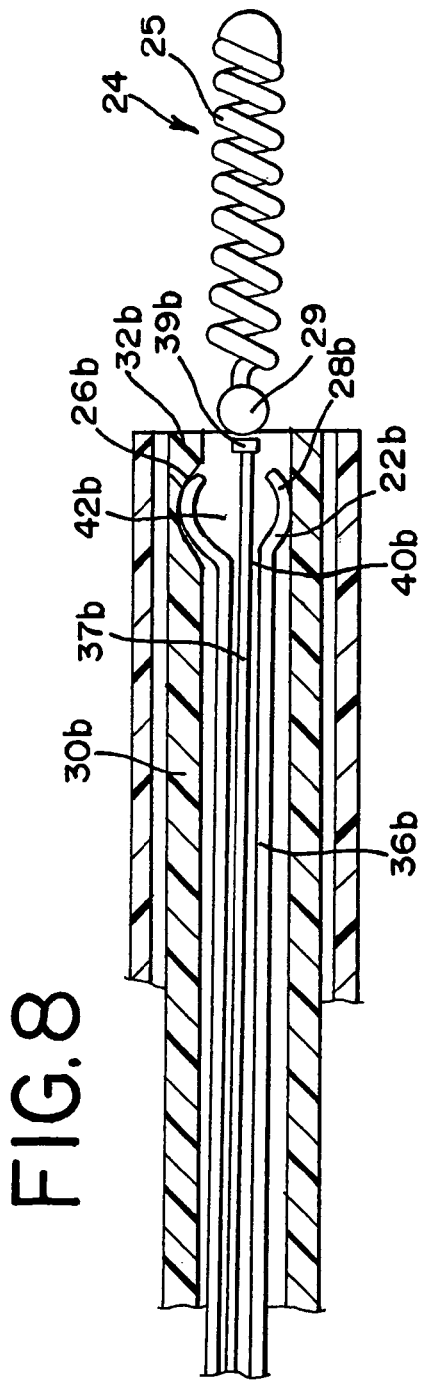

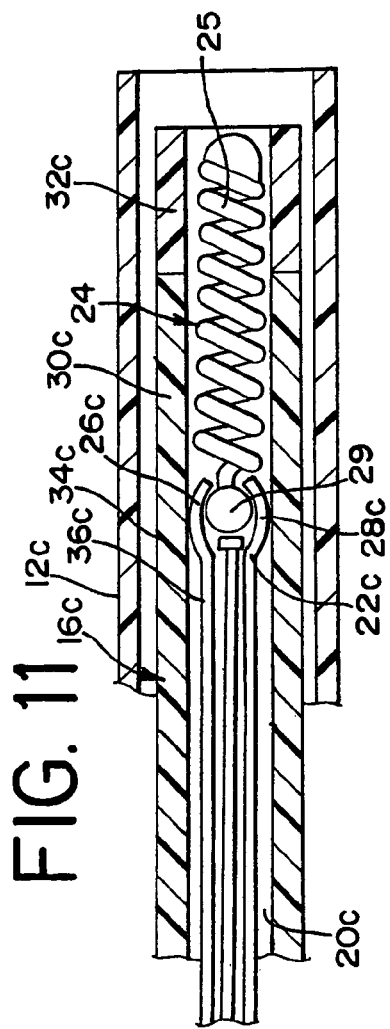
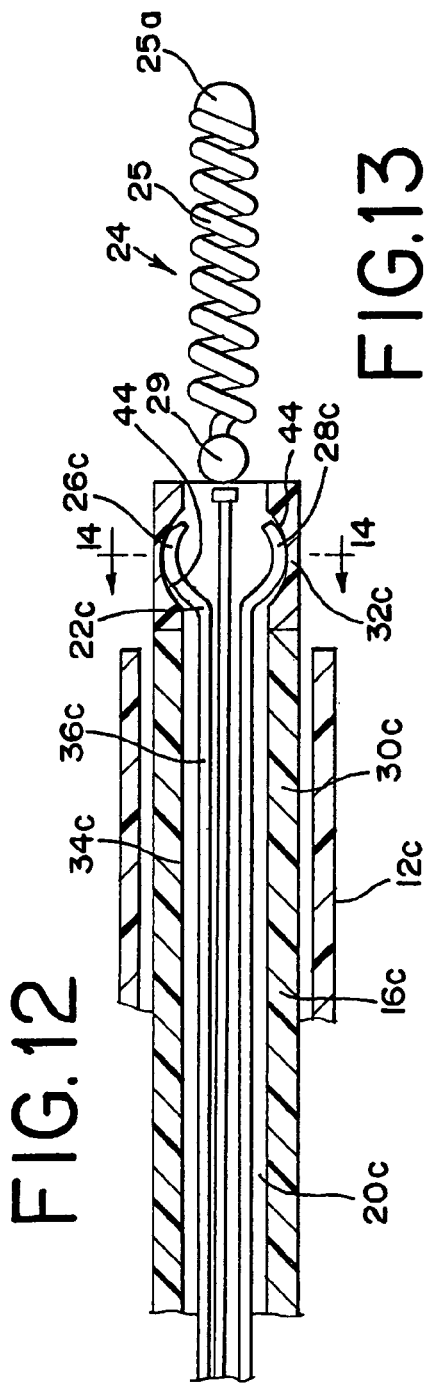
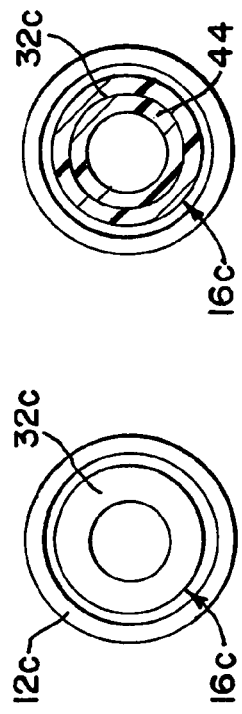

EMBOLIC DEVICE DELIVERY SYSTEM

FIELD OF THE INVENTION

The present invention is related to the delivery of embolic occlusion devices. Disclosed are occlusion device deployment systems and methods for mechanically deploying occlusion devices at a preselected location within a patient, in an accurate and rapid manner. The deployment systems and methods are particularly well suited for deploying an embolic coil at a location of concern within the vasculature, especially intracranially, of a patient.

BACKGROUND OF THE INVENTION

The use of catheter delivery systems for positioning and deploying therapeutic devices, such as dilation balloons, stents and embolic coils, in the vasculature of the human body has become a standard procedure for treating endovascular diseases. It has been found that such devices are particularly useful in treating areas where traditional operational procedures are impossible or pose a great risk to the patient, for example in the treatment of aneurysms in intracranial blood vessels. Due to the delicate tissue surrounding intracranial blood vessels, especially for example brain tissue, it is very difficult and often risky to perform surgical procedures to treat defects of intracranial blood vessels. Advancements in catheter deployment systems have provided an alternative treatment in such cases. Some of the advantages of catheter delivery systems are that they provide methods for treating blood vessels by an approach that has been found to reduce the risk of trauma to the surrounding tissue, and they also allow for treatment of blood vessels that in the past would have been considered inoperable.

Typically, these procedures involve inserting the distal end of a delivery catheter into the vasculature of a patient and guiding it through the vasculature to a predetermined delivery site. A vascular occlusion device, such as an embolic coil, is attached to the end of a delivery member which pushes the occlusion device through the catheter and out of the distal end of the catheter into the delivery site. Some of the problems that have been associated with these procedures relate to the accuracy of occlusion device placement. For example, the force employed to eject the occlusion device from the delivery catheter may cause the occlusion device to over shoot the predetermined site or dislodge previously deployed occlusion devices. Also, once the occlusion device is pushed out of the distal end of the catheter, the occlusion device cannot be retracted and may migrate to an undesired location. Often, retrieving and repositioning the occlusion devices requires a separate procedure and has the potential to expose the patient to additional risk.

In response to the above mentioned concerns, numerous devices and release mechanisms have been developed in an attempt to create delivery systems which provide both control of an occlusion device after the device has exited the delivery catheter and a rapid release or detachment mechanism to release the device once the occlusion device is in place. One such device is disclosed in Geremia et al. U.S. Pat. No. 5,108,407, which shows a fiber optic cable including a connector device mounted at the distal end of the fiber optic cable. An embolic coil is attached to the connector device by a heat releasable adhesive. Laser light is transmitted through the fiber optic cable to increase the temperature of the connector device, which melts the adhesive and releases the embolic coil. One drawback to using this type of system is the potential risk of melted adhesives contaminating the blood stream.

Another coil deployment system employs a pusher member having an embolic coil attached to the pusher member by a connector fiber which is capable of being broken by heat, as disclosed in Gandhi et al. U.S. Pat. No. 6,478,773. The pusher member of this arrangement includes an electrical resistance heating coil through which the connector fiber is passed. Electrical current is supplied to the heating coil by a power source connected to the heating coil via wires extending through an internal lumen of the pusher. The power source is activated to increase the temperature of the heating coil which breaks the connector fiber. One drawback is that connecting the resistance heating coil to the power source requires running multiple wires through the pusher member. Additionally, the electrical current traveling through the wires may create stray electromagnetic fields that have the potential to interfere with other surgical and monitoring equipment.

Yet another embolic coil positioning and delivery system is described in Saadat et al. U.S. Pat. No. 5,989,242, which discloses a catheter having a shape memory alloy connector attached to the distal end of the catheter. The connector includes a socket having a pair of spaced-apart fingers which are responsive to a change in temperature. The fingers are bent towards each other and hold a ball which is connected to an end of an embolic coil. The connector absorbs laser light transmitted through an optical cable and transforms the light into heat energy. The heat energy raises the temperature of the connector and opens the fingers, thereby releasing the embolic coil. This type of ball and socket connection is rigid and causes the catheter to be stiff, making it difficult to guide the catheter through the vasculature of the body. This patent, and all other patents and references identified herein are hereby incorporated herein by reference.

Further, the above-identified delivery systems typically require electronic equipment powered by a power source. If the electronic equipment is defective or the power source fails, the procedure may be prolonged while the equipment is repaired or replaced. Prolonging the procedure may expose the patient to additional risk.

Despite these advances, a need remains for a rapid release vascular occlusion deployment system and/or method that can function without electrical equipment or a power supply, does not develop chemical debris, is simple to manufacture, flexible and easy to guide through the vasculature of the body, provides excellent control over the occlusion device, and reduces the possibility of interference with other surgical and/or monitoring equipment.

SUMMARY OF INVENTION

The present invention embodies deployment systems and methods for accurately and rapidly deploying an embolic device at a location of concern within a patient. A full deployment system can employ an elongated flexible delivery catheter for guiding a deployment unit to a location of concern within a patient.

The deployment unit includes a tubular element for guiding the embolic device, such as an embolic coil, through the delivery catheter to the location of concern. In one embodiment, the tubular element has a proximal end portion, a distal end portion and a lumen extending along the tubular element. A catch is movably located within the lumen of the tubular element. The catch has a closed configuration and an open configuration, with the catch being biased to be in the open configuration. In the closed configuration, the catch is able to grasp or hold a portion of an embolic element. In the open configuration, the catch releases its grasp of the embolic element.

The tubular element includes a constraining portion and a releasing portion. When the catch is within the constraining portion of the tubular element, the constraining portion acts on the catch to keep the catch in the closed configuration. When the catch is moved into the releasing portion, the catch is free to return to its biased open configuration.

According to one preferred method of the present invention, an embolic device headpiece is inserted into an open catch. The catch is closed so that the catch grasps or holds the embolic device headpiece. The catch is then inserted into the constraining portion of the tubular element where the inner wall of the constraining portion acts on the catch to keep it in the closed configuration.

The tubular element is then employed to manipulate the embolic device through the delivery catheter to a deployment site within a patient. Once the embolic device is positioned at the deployment site, the catch is moved into the releasing portion of the tubular element where the catch is no longer inhibited by the tubular element and free to return to its biased open configuration. In the open configuration, the catch releases its grasp on the embolic device headpiece. In one embodiment, the catch can also be used to push the embolic element out of the tubular element. Optionally, the delivery apparatus can include a separate pushing element for such purpose.

Other aspects, objects and advantages of the present invention will be understood from the following description according to the preferred embodiments of the present invention, specifically including stated and unstated combinations of the various features which are described herein, relevant information concerning which is shown in the accompanying drawings.

BRIEF DESCRIPTION OF THE DRAWINGS

In describing the preferred embodiments of the present invention, reference will be made to the accompanying drawings, wherein:

FIG. 1 is an enlarged partially sectioned view of an embolic device deployment system in accordance with a preferred embodiment of the present invention shown prior to deployment of the embolic device;

FIG. 2 is an enlarged partially sectioned view of the embolic device deployment system of FIG. 1 shown after the embolic device has been deployed;

FIG. 3 is a cross-sectional view of the deployment unit of FIG. 1 taken in the direction indicated by line 3-3 of FIG. 1;

FIG. 4 is an enlarged partially sectioned view of another embolic device deployment system shown prior to deployment of the embolic device;

FIG. 5 is an enlarged partially sectioned view of the embolic device deployment system of FIG. 4 shown after the embolic device has been deployed;

FIG. 6 is a cross-sectional view of the deployment unit of FIG. 4 taken in the direction indicated by line 6-6 of FIG. 4, omitting the guide catheter and embolic device shown in FIG. 4;

FIG. 7 is an enlarged partially sectioned view of yet another embodiment of the embolic device deployment system shown prior to deployment of the embolic device;

FIG. 8 is an enlarged partially sectioned view of the embolic device deployment system of FIG. 7 shown after the embolic device has been deployed;

FIG. 9 is a cross-sectional view of the deployment unit of FIG. 7 taken in the direction indicated by line 9-9 of FIG. 7, omitting the guide catheter and embolic device shown in FIG. 7;

FIG. 10 is a cross-sectional view of yet another embodiment of the tubular element of an embolic deployment system wherein the indent extends circumferentially all the way around the inner wall of the tubular element;

FIG. 11 is an enlarged partially sectioned view of yet another embodiment of the embolic device deployment system shown prior to deployment of the embolic device;

FIG. 12 is an enlarged partially sectioned view of the embolic device deployment system of FIG. 11 shown after deployment of the embolic device;

FIG. 13 is an end elevational view of the system illustrated in FIG. 11, omitting the embolic device; and FIG. 14 is a cross-sectional view along the line 14-14 of FIG. 12, omitting the embolic device.

DESCRIPTION OF THE PREFERRED EMBODIMENTS

As required, detailed embodiments of the present invention are disclosed herein; however, it is to be understood that the disclosed embodiments are merely exemplary of the invention, which may be embodied in various forms. Therefore, specific details disclosed herein are not to be interpreted as limiting, but merely as a basis for the claims and as a representative basis for teaching one skilled in the art to variously employ the present invention in virtually any appropriate manner.

FIG. 1 generally illustrates a preferred embodiment of the occlusion device deployment system of the present invention. The deployment system, generally designated at 10, can include an elongated flexible delivery or guide catheter 12 which can be inserted into the vasculature of a patient and used to guide a deployment unit, generally designated at 14, to a preselected site in a manner generally known in the art. One of ordinary skill in the art will appreciate that the delivery catheter 12 and the deployment unit 14 are much longer than illustrated in the figures.

The deployment unit 14 includes an elongated tubular element 16 which has a proximal end portion (not shown) and a distal end portion 18. A lumen 20 extends along the tubular element 16 from the proximal end portion to the distal end portion 18. A catch 22 is located within the lumen 20 and is movable proximally and distally within the lumen. The catch 22 releasably attaches an embolic device 24 to the delivery unit 14.

Referring to FIGS. 1 and 2, the catch 22 may include a first jaw 26 and a second jaw 28. The first and second jaws 26, 28 may be opposed jaws in a clamshell configuration. The catch 22 has an open configuration (shown in FIG. 2) at which it is biased or set during manufacture or treatment. Catch 22 also has a closed configuration (shown in FIG. 1). The catch 22 is normally biased to the open configuration by a spring mechanism (not shown) by the resiliency of the catch material, and/or by the design of the catch. As illustrated in FIG. 1, in the closed configuration, the jaws 26, 28 can grasp and hold a headpiece 29 of the embolic device 24.

The tubular element 16 includes a first or constraining section 30 and a second or release section 32. Referring to FIG. 1, while in the constraining section 30, the inner wall 34 of the tubular element 16 acts upon the catch 22 to exert force upon the catch, which is typically radially inwardly directed, in order to maintain the catch in the closed position. In this particular embodiment, the inner wall 34 of the tubular element 16 contacts the first and second jaws 26, 28 and keeps them in the closed configuration. As illustrated in FIGS. 2 and 3, the release section 32 can include a pair of apertures 35, 35a. When the catch is moved into the release section 32, the now unconstrained jaws 26, 28, under the force of their natural bias, enter the apertures 35, 35a and move apart into the open configuration.

An elongated member 36, such as a wire, is attached to the catch 22. The elongated member 36 can be used to move the catch 22 proximally and distally within the lumen 20, between the constraining and releasing sections 30, 32 of the tubular element 16. When the catch 22 is moved from the constraining section 30 into the release section 32 of the tubular element 16, the catch 22 opens and releases its grasp of the embolic device headpiece 29.

The operation of the embolic device deployment system will now be generally described with respect to FIGS. 1 and 2. To attach the embolic device 24 to the delivery unit 14, the embolic device headpiece 29 is placed between jaws 26 and 28 of the catch 22. The elongated member 36 is then employed to pull the catch 22 into the constraining section 30 of the tubular element. As described above, while in the constraining section 30, the inner wall 34 of the tubular element 16 acts upon the catch 22 to keep jaws 26 and 28 in the closed configuration. In the closed configuration, the catch 22 grasps the embolic device headpiece 29 to attach the embolic device 24 to the delivery unit 14.

After the embolic device 24 has been attached to the delivery unit 14, the delivery catheter 12 can be inserted into the vasculature system of a patient, and the distal end portion of the catheter can be positioned at a preselected location within a blood vessel, typically in conjunction with other devices and professional procedures as generally known in the art. The delivery unit 14 is inserted into a proximal end portion of the catheter 12, and the delivery unit 14 is advanced through the delivery catheter 12 until the embolic device 24 reaches the distal end portion of the delivery catheter 12.

Referring to FIG. 2, once the embolic device 24 reaches the distal end portion of the delivery catheter 12, the embolic device 24 may be moved out of the distal end portion of the delivery catheter 12 by moving the delivery catheter in a retrograde manner as indicated by arrow B, by advancing the tubular element 16 as indicated by arrow C, or by a combination of moving the delivery catheter in a retrograde manner and advancing the tubular element.

The embolic device 24 preferably includes at least one radiopaque marker, such as its tip 25a, so that the position of the embolic device can be monitored by fluoroscopy or the like. Alternatively, substantially all of the embolic device can have radiopaque properties, such as having a platinum or a platinum alloy make-up. After the embolic device 24 has exited the delivery catheter 12, if it is determined that the embolic device 24 is in the wrong position and/or a different embolic device is required, the tubular element 16 can be retracted to move the embolic device 24 back into the delivery catheter 12. Once in the delivery catheter 12, the embolic device can be repositioned or completely removed from the patient.

After it has been determined that the embolic device 24 is at the desired location within the patient, the elongated member 36 is moved proximally within the tubular element 16 to move the catch 22 into the release section 32. While in the release section 32, the jaws 26 and 28 of the catch 22 move to their biased open position and release their grip on the embolic headpiece 29. The delivery catheter 12 and the tubular element 16 may then be moved proximally to deploy the embolic device 24.

After the release, the delivery unit 14 can now be retracted through the delivery catheter 12 and removed from the patient. If desired, additional embolic devices may be deployed in a similar manner to that described above. For example, multiple embolic devices can be delivered to an intracranial aneurysm.

FIGS. 4, 5 and 6 illustrate another embodiment of the embolic device delivery system in accordance with the present invention. The embolic device delivery system, generally designated 10a, can include a delivery catheter 12a and a tubular element 16a. The tubular element 16a has an inner wall 34a that defines an inner lumen 20a. A catch 22a, similar to the catch described above, is located within the lumen 20a and has jaws 26a and 28a which can grasp an embolic device headpiece 29 when in the closed configuration. An elongated member 36a is connected to the catch 22a and can be employed to move the catch proximally and distally within the lumen.

Referring to FIGS. 4 and 6, the tubular element 16a includes a constraining section 30a and a release section 32a. The constraining section 30a is similar to the constraining section 30 described above. In this embodiment, constraining section 30a is proximal of the release section 32a. The inner cross-section extent "C" of the constraining section 30a is such that the inner wall 34a of the tubular element 16a contacts jaws 26a and 28a of catch 22a to keep them in a closed configuration. The release section 32a has cross-sectional extent "R" that is larger than the cross-sectional extent C. Referring to FIG. 5, the cross-sectional extent R is sufficiently large to allow jaws 26a and 28a of the catch 22a to move to their normally biased open position, thereby releasing embolic device headpiece 29 and thus the embolic device.

FIGS. 7, 8 and 9 illustrate yet another embodiment of the embolic device delivery system in accordance with the present invention. The embolic device delivery system 10b can include a delivery catheter 12b and a tubular element 16b. The tubular element 16b has an inner wall 34b that defines an inner lumen 20b. A catch 22b, having similar features as described above, is located within the lumen 20b.

The catch 22b can include opposed jaws 26b and 28b which are normally biased to an open configuration. A first elongated member 36b in the form of a hollow shaft or tube can be connected to the catch 22b and can be employed to move the catch proximally and distally within the lumen 20b. A second elongated member 37b, such as a wire pusher, is located within the first elongated member 36b. The first elongated member 36b and the second elongated member 37b can have a shaft within a shaft configuration where they can be moved in conjunction with or independently of one another. The second elongated member 37b has a distal end 39b which can extend through an opening 40b into the space 42b between the jaws 26b, 28b of the catch 22b. The second elongated member 37b can be advanced distally through the first elongated member 36b so that the distal end 39b of the second elongated member contacts the embolic headpiece 29 and pushes it out of the catch 22b when the headpiece is not grasped by the jaws.

The tubular element 16b includes a constraining section 30b and a release section 32b. The constraining section 30b is similar to the constraining section 30a described above and has an inner cross-sectional extent "C" such that the inner wall 34b of the tubular element 16b contacts the catch 22b to keep it in a closed configuration. Referring to FIG. 8, the release section 32b includes an indent 33b that is sized and shaped, such as being wide enough and deep enough to allow at least one of the jaws 26b, 28b to move to its open configuration. In the illustrated embodiment, indent 33b receives jaw 26b. As illustrated in FIG. 9, the indent 33b preferably extends circumferentially at least half way along the inner wall of the tubular element so as to form a generally semicircular groove. Referring to FIG. 10, it is also contemplated that an indent 43 could be provided that extends circumferentially all the way around the inner surface of the inner wall of the tubular element to provide a substantially circular groove.

FIGS. 11, 12, 13 and 14 illustrate yet another alternative embodiment of the embolic device delivery system in accordance with the present invention. The embolic device delivery system 10c can include a delivery catheter 12c and a tubular element 16c. The tubular element 16c has an inner wall 34c that defines an inner lumen 20c. A catch 22c having similar features to catch 22 or 22b is located within the lumen 20a. As described above, an elongated member 36c can be employed to move the catch 22c proximally and distally within the lumen.

The tubular element 16c includes a constraining section 30c and a release section 32c. The constraining section 30c is similar to the constraining sections 30, 30a and 30b as described above. The release section 32c of this embodiment comprises a pliable section that can be secured to the constraining section 30c or an integral component thereof that is the result of extrusion techniques or treatments of the constraining section and/or the release section.

However it is formed or provided, the pliable release section 32c is sufficiently deformable so that when the catch 22c is moved into the release section 32c, one or both of the jaws 26c and 28c of the catch 22c are allowed to open. In other words, the biasing force of the jaws 26c, 28c to the open position is greater than the constraining force of the pliable release section 32c such that jaws open and deform the inner wall 34c of the release section to provide an indented area 44. Such an indented area is adequate to release the grasp of the jaws 26c and 28c on the headpiece 29.

The operation of the embolic device deployment systems illustrated in FIGS. 4-14 will now be generally described with respect to FIGS. 4 and 5. To attach the embolic device 24 to the delivery unit 14a, the embolic device headpiece 29 is placed between jaws 26a and 28a of the catch 22a. The elongated member 36a is then employed to position the catch 22a into the tubular element's constraining section 30a. As described above, while in the constraining section 30a, the inner wall 34a of the tubular element 16a acts upon the catch 22a to keep jaws 26a and 28a in the closed configuration. In the closed configuration, the catch 22a grasps the embolic device headpiece 29 to attach the embolic device 24 to the delivery unit 14a.

After the embolic device 24 has been attached to the delivery unit 14a, the delivery catheter 12a can be inserted into the vasculature system of a patient, and the distal end portion of the catheter can be positioned at a preselected location within a blood vessel, as described above. The delivery unit 14a is inserted into a proximal end portion of the catheter 12a, and the delivery unit 14a is advanced through the delivery catheter 12a until the distal end portion of the tubular element reaches the distal end portion of the delivery catheter 12.

Referring to FIG. 5, once the distal end portion of the tubular element 16a reaches the distal end portion of the delivery catheter 12a, the embolic device 24 may be partially moved out of the distal end portion of the delivery catheter 12a and the tubular element 16a by moving the delivery catheter and the tubular element in a retrograde manner as indicated by arrow B, by advancing the elongated member 36a as indicated by arrow C, or by a combination of moving the delivery catheter in a retrograde manner and advancing the elongated member.

The embolic device 24 preferably includes at least one radiopaque marker so that the position of the embolic device can be monitored by fluoroscopy. After the embolic device 24 has partially exited the delivery catheter 12a and the tubular element 16a, but before the catch 22a has been moved into the release section 32a, if it is determined that the embolic device 24 is in the wrong position and/or a different embolic device is required, the tubular element 16 can be retracted to move the embolic device 24 back into the delivery catheter 12a. Once in the delivery catheter 12a, the embolic device can be repositioned or completely removed from the patient.

After it has been determined that the embolic device 24 is at the desired location within the patient, the elongated member 36a is moved distally within the tubular element 16a to move the catch 22a into the release section 32a. While in the release section 32a, the biased jaws 26a and 28a of the catch 22a move to or toward their normal open position and release their grip on the embolic headpiece 29. The delivery catheter 12a and the tubular element 16a may then be moved proximally to deploy the embolic device 24. Alternatively, the elongated member 36a could be advanced further distally so that the catch 22a acts a pusher that pushes the embolic device 24 out of the distal ends of tubular element 16a and delivery tube 12a. In yet another alternative, such as in the embolic device delivery system of FIG. 8, the second elongated member 37b can be moved distally within the first element member 37b so that the distal end 39b the second elongated member contacts the embolic device headpiece 29 and pushes it from the catch 22b.

After the release, the delivery unit 14a can now be retracted through the delivery catheter 12a and removed from the patient. If desired, additional embolic devices may be deployed in a similar manner to that described above.

The tubular elements 16, 16a, 16b and 16c can be any suitable type of delivery tube generally known in the art that has sufficient column strength to guide an embolic device through a delivery catheter and has sufficient flexibility to be guided through tortuous pathways within the vasculature of a patient. For example, the delivery tube can be comprised of a flexible polymer sheath.

The elongated member 36 is preferably a wire that is comprised of a metallic or polymeric material which has tensile and flex properties that allow the elongated member 36 to be easily guided through tortuous paths within the patient. The elongated member 36 should also have sufficient structural integrity to allow pushing and pulling of the elongated member 36 to move the catch 22.

The embolic device 24 is preferably an embolic device assembly that includes an embolic element 25 and a headpiece 29. As illustrated, the embolic device headpiece 29 can be a ball shaped structure located at the proximal end of the embolic element 25. The ball shaped headpiece is of a size and shape to be received into the closed catch 22 and can be released from the open catch 22. The embolic device can comprise a headpiece and the embolic element which are separate components that are secured together. Alternatively, the embolic element 25 and the headpiece 29 can be of a unitary construction.

The embolic element 25 is preferably an embolic coil which can be of the type which takes a substantially linear configuration for being advanced through the delivery catheter 12 and a more randomly oriented relaxed condition after it is released from the catheter. Alternatively, the embolic element may be any other type of embolic element which may take on various forms and configurations, such as hydrogels, foams, bioactive coils, braids, cables and hybrid devices.

It will be understood that the embodiments of the present invention which have been described are illustrative of some of the applications of the principles of the present invention. Numerous modifications may be made by those skilled in the art without departing from the true spirit and scope of the invention, including those combinations of features that are individually disclosed or claimed herein.

The invention claimed is:

1. An embolic device deployment system, comprising:
   a tubular element having an outer wall, an inner wall defining a lumen, and a wall thickness between the outer and inner walls of the tubular element;
   a catch movably located within said lumen, the catch comprising a pair of jaws, at least one of said jaws is biased toward an open position providing a spacing between the jaws which is greater than spacing between the jaws at said closed position, the catch having a closed position, said catch being biased to the open position and sized to hold a portion of an embolic element when in the closed position;
   said tubular element having a constraining section which constrains the catch to the closed position and a release section which permits the catch to move toward the open position when the catch is located at the release section;
   said constraining section has a distal end edge at the distal-most location of the tubular element, a distal portion that is located distally of the release section, and a proximal portion that is located proximally of the release section;
   said release section comprises a pair of generally opposing apertures that are each between said distal and proximal portions of the constraining section;
   each aperture of the pair of apertures is an opening completely through said wall thickness of the tubular element to effect said open position at which one said pair of jaws enters one of said pair of apertures and the other of said pair of jaws enters the other of said pair of apertures to release the embolic device; and
   said constraining section distal portion of the tubular element is a tubular portion that is a cylinder distal of the apertures that extends for a length of the tubing between the distal-end edge of the tubular element and the distal-most extent of the apertures, said constraining section cylinder distal of the apertures is proximal of the distal-end edge thereby allowing the catch to move to the open configuration when proximal of the distal-end edge of the tubular element, thereby releasing the embolic device into the cylinder distal of the apertures.

2. The deployment system of claim 1 wherein the pair of apertures extend circumferentially along the tubular element.

3. The deployment system of claim 1 wherein said constraining section and said release section are spaced longitudinally from each other along said tubular element, further including an elongated member attached to the catch whereby the elongated member is used to move the catch within the lumen between at least said constraining section and said release section.

4. The deployment system of claim 3 wherein the elongated member includes a lumen and a second elongated member located within the lumen, said second elongated member being movable linearly within the lumen and having a distal end portion which extends into the catch.

5. A combination of an embolic device and an embolic device deployment system, comprising:
   an embolic device;
   a tubular element having an outer wall, an inner wall defining a lumen, and a wall thickness between the outer and inner walls of the tubular element;
   a catch movably located within said lumen, the catch comprising a pair of jaws, at least one of said jaws is biased toward an open position providing a spacing between the jaws which is greater than spacing between the jaws at said closed position, the catch having a closed position, said catch being biased to the open position, said catch grasping a portion of the embolic device when in the closed position and releasing the portion of the embolic device when in the open position;
   said tubular element having a constraining section which constrains the catch to the closed position and a release section which permits the catch to move toward the open position when the catch is located at the release section to thereby release the embolic device;
   said constraining section has a distal end edge at the distal-most location of the tubular element, a distal portion that is located distally of the release section, and a proximal portion that is located proximally of the release section;
   said release section comprises a pair of generally opposing apertures that are each between said distal and proximal portions of the constraining section;
   each aperture of the pair of apertures is an opening completely through said wall thickness of the tubular element to effect said open position at which one said pair of jaws enters one of said pair of apertures and the other of said pair of jaws enters the other of said pair of apertures to release the embolic device; and
   said constraining section distal portion of the tubular element is a tubular portion that is a cylinder distal of the apertures that extends for a length of the tubing between the distal-end edge of the tubular element and the distal-most extent of the apertures, said constraining section cylinder distal of the apertures is proximal of the distal-end edge thereby allowing the catch to move to the open configuration when proximal of the distal-end edge of the tubular element, thereby releasing the embolic device into the cylinder distal of the apertures.

6. The combination of claim 5 wherein the pair of apertures extend circumferentially along the tubular element.

7. The combination of claim 5 further including an elongated member attached to the catch whereby the elongated member is used to move the catch within the lumen.

8. The combination of claim 7 wherein the elongated member includes a lumen and a second elongated member located within the lumen, said second elongated member being movable linearly within the lumen and having a distal end portion which extends into the catch.

9. A method of delivering an embolic device to a location within the vasculature of a patient, comprising:
   providing a tubular element having a wall thickness defined between an outer wall and an inner wall defining a lumen, the tubular element having a distal end edge, a catch having a closed position and being movably located within the lumen, the catch comprising a pair of jaws, at least one of the jaws is biased toward an open position providing a spacing between the jaws which is greater than spacing between the jaws at said closed position, grasping a portion of the embolic device when in the closed position and releasing the portion of the embolic coil when in the open position, the tubular element having a constraining section which constrains the catch to the closed position and a release section having a pair of generally opposing apertures completely through the wall thickness of the tubular element and that permit the catch to move into the apertures and toward the open position, the constraining section is tubular and extends from the distal end edge of the tubular element to the apertures to form a cylinder that is distal of the apertures;
   inserting a portion of an embolic device into the catch;

positioning the catch within the constraining section of the tubular element to maintain the catch in a closed position;

manipulating the tubular element to guide the embolic device to a preselected location within the vasculature of a patient;

moving the catch along the tubular constraining section until one of the pair of jaws of the catch enters into one of the pair of apertures of the release section of the tubular element and until the other jaw enters the other aperture, said moving being to the constraining section cylinder distal of the apertures, which is at a location proximal of the distal end edge thereby allowing the catch to move to the open configuration when proximal of the distal end edge of the tubular element, thereby releasing the embolic element into the cylinder distal of the apertures; and allowing relative longitudinal movement between the tubular element and the embolic element until the embolic device fully exits from the cylinder distal of the apertures.

10. The method of claim 9 further including an elongated member attached to the catch, and the moving comprises manipulating the elongated member to move the catch longitudinally between at least the constraining section and the release section.

* * * * *